United States Patent [19]

Zupon et al.

[11] Patent Number: 4,469,228

[45] Date of Patent: Sep. 4, 1984

[54] INTERFERON KIT

[75] Inventors: Michael A. Zupon, Madison, N.J.; Joel A. Sequeira, New York, N.Y.; Alan S. Kirschner, East Brunswick; Pui-Ho Yuen, Edison, both of N.J.

[73] Assignee: Schering Corporation, Madison, N.J.

[21] Appl. No.: 499,138

[22] Filed: May 31, 1983

[51] Int. Cl.³ .............................................. B65D 81/32
[52] U.S. Cl. .................................... 206/568; 206/568; 206/219
[58] Field of Search ............................... 206/219, 568

[56] References Cited

U.S. PATENT DOCUMENTS

| 2,893,547 | 7/1959 | Earl et al. | 206/219 |
| 3,064,802 | 11/1962 | Jess et al. | 206/219 |
| 3,240,328 | 3/1966 | Matteuzzi | 206/219 |
| 3,616,543 | 11/1971 | Barclay | 206/568 |
| 3,893,280 | 7/1975 | King | 206/568 |
| 4,089,432 | 5/1978 | Crankshaw et al. | 206/219 |

Primary Examiner—William T. Dixson, Jr.
Attorney, Agent, or Firm—Stephen I. Miller; Bruce M. Eisen

[57] ABSTRACT

Disclosed is a kit for preparing a lyophilized alpha interferon gel formulation suitable for topical administration.

5 Claims, 13 Drawing Figures

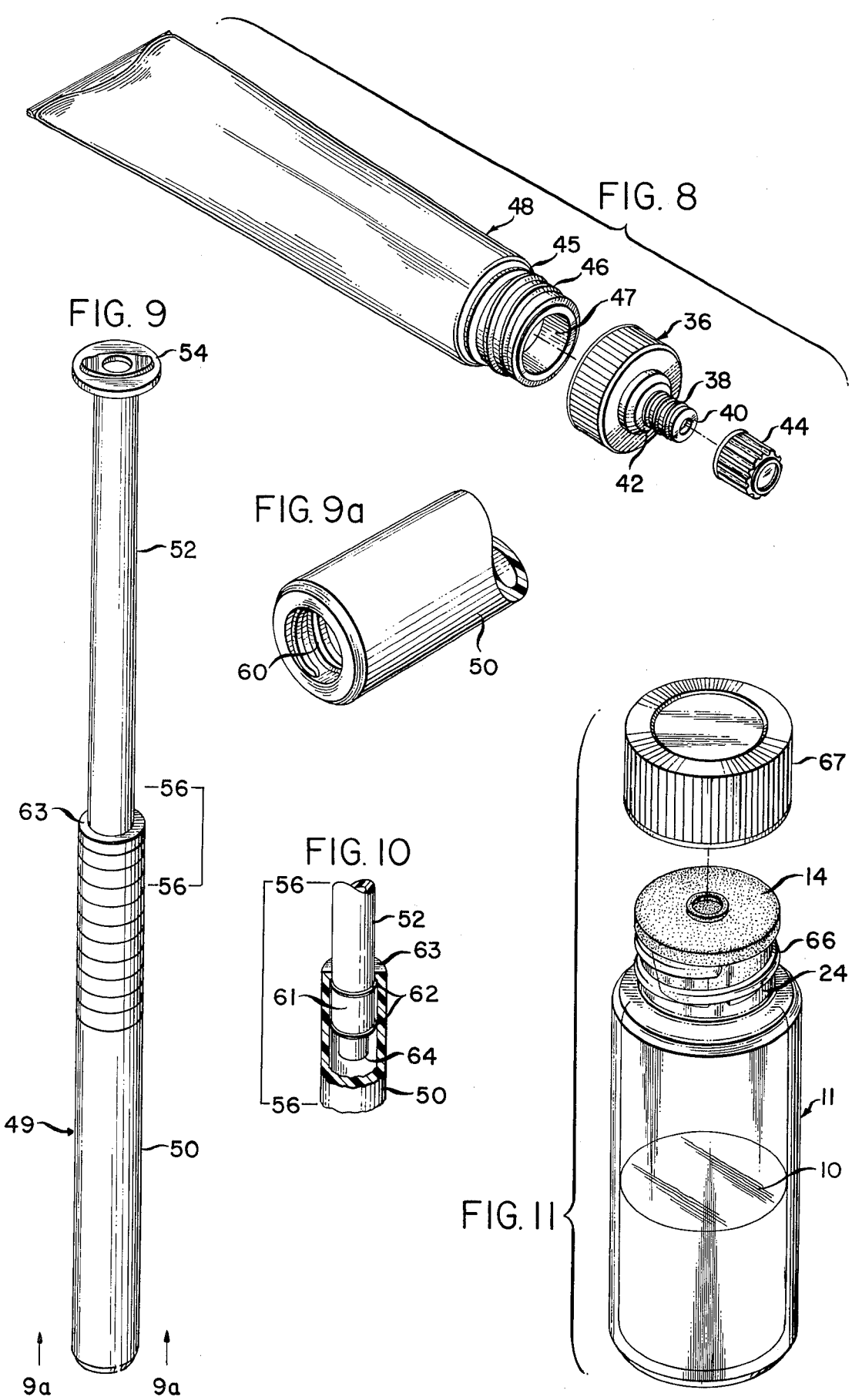

INTERFERON KIT

This invention relates to a kit with which one may prepare and topically administer a lyophilized alpha type interferon gel.

It is widely believed that alpha type interferons, applied topically, have great potential as a drug for the treatment of a wide variety of disease states and particularly for various types of viral infection, e.g. herpes. Alpha type interferon itself is unstable over an extended period of time in an aqueous solution and in order to minimize decomposition of the alpha type interferon during storage, the aqueous solution is lyophilized. The lyophilized alpha type interferon is reconstituted with water immediately prior to administration. Topical administration of the reconstituted lyophilized alpha type interferon was thought to be impractical since the resulting reconstituted formulation lacks sufficient consistency for these applications.

We have developed a kit for easy constitution of a lyophilized alpha type interferon gel suitable for topical application. Combining the dermatologically acceptable vehicle of this kit with the lyophilized alpha type interferon powder surprisingly results in an elegant gel formulation. In particular, the present invention pertains to a kit for formulating and dispensing an alpha type interferon gel composition comprising (a) a vial having an open end aseptically sealed and containing about $1 \times 10^4$ to $5 \times 10^8$ International Units of lyophilized alpha type interferon formulation prepared from an alpha type interferon having a specific activity of at least $5 \times 10^7$ International Units/mg total protein; and (b) a tube with flexible walls having a sealed open end containing a dermatologically acceptable vehicle which contains a compatible preservative and a sufficient amount of polyoxyethylene polyoxypropylene block polymer for the vehicle to be a liquid at about 15° C. and below and which together with the lyophilized alpha type interferon gels at about 15° C. and above.

As used herein, the term "alpha type interferon" means an interferon exhibiting biological properties similar to those of human leucocyte interferon. It should be noted that a number of human alpha interferon species are known, usually designated by a numeral after the Greek letter. Also included within the scope of this invention are the so called alpha hybrid interferons wherein fragments of two native alpha interferon species are joined (see for instance, EP No. 51873). Preferred forms of alpha interferon for use in the formulations of the present invention are alpha-1 and alpha-2 interferon. Most preferably, the formulations of the present invention employ alpha-2 interferon which may be prepared by recombinant-DNA methods for example, those disclosed by Nagata et al., Nature, 284, 316–320 (1980).

By the term "topical" it is meant that the gel is suitable for vaginal, ophthalmic, rectal and dermal administration.

The term "dermatologically acceptable vehicle" means pharmaceutical vehicles which are substantially non-toxic and non-irritating to the skin, eyes, or mucous membranes depending on the intended site of administration.

BRIEF DESCRIPTION OF THE DRAWINGS

FIG. 8 illustrates the various components which comprise the tube with flexible walls found in the kit of the present invention.

FIG. 9 illustrates an applicator adaptable to fit onto the tube with flexible walls and is suitable for topical vaginal application of the alpha type interferon gel formulation.

FIG. 9a illustrates an end view of the applicator taken along section 9a—9a of FIG. 9.

FIG. 10 is a sectional view taken along Section 56—56 of FIG. 9.

FIG. 11 illustrates an alternative vial for the kit of the present invention.

DETAILED DESCRIPTION OF THE DRAWINGS

Figure 1:
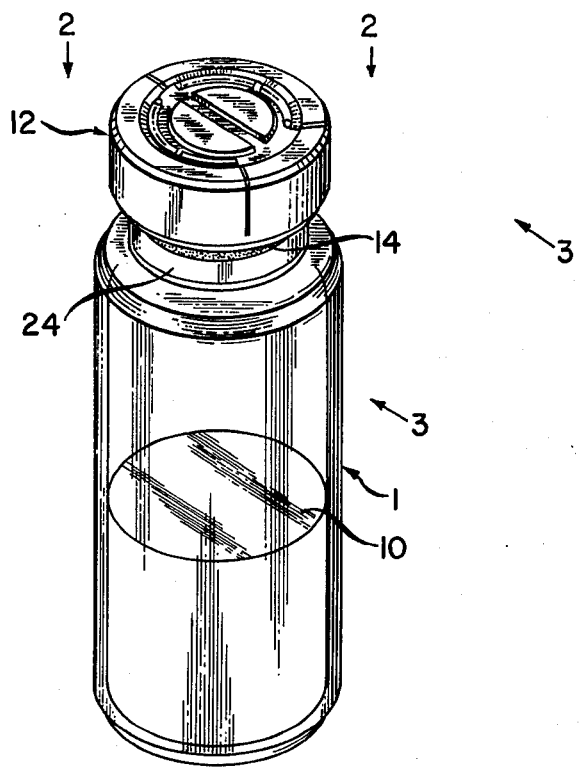
FIG. 1 is an isometric view of the aseptically covered vial found in the kit of the present invention.

Vial 1 of FIG. 1 contains a lyophilized alpha type interferon formulation 10. Vial 1 also contains a rubber or plastic stopper 14 extending into the neck 24 of the vial 1 and which is overfitted with a metallic cap 12.

Figure 2:
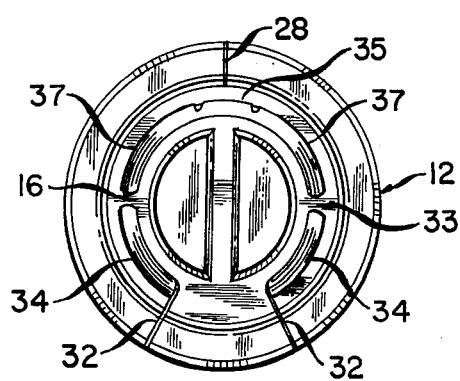
FIG. 2 is a top view of the vial cover taken along section 2—2 of FIG. 1.
Figure 3:
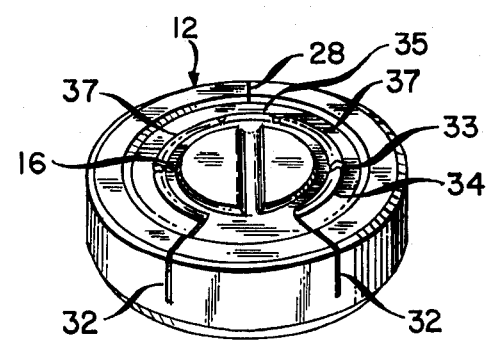
FIG. 3 is an isometric view of the same vial cover taken along section 3—3 of FIG. 1.

FIG. 2 and FIG. 3 illustrate metallic cap 12 taken along section 2—2 of FIG. 1 and section 3—3 of FIG. 1. Metallic cap 12 contains two cuts 32 which are attached to two curved cuts 34. Metallic cap 12 also contains cut 28 at the rear of the cap. Curved cuts 34 are separated from a semicircular cut 37 by hinges 33. Cuts 34 and 37 thus define a perforated ring 16 extending partway around the top of cap 12. Hinges 33 serve as a means for attaching ring 16 to the remainder of the cap 12. Ring 16 serves as an inner pull tab attached to an outer crimp portion 18 by hinges 33 and bridges at the bottom of cuts 32. The hinges 33 are easily broken allowing for facile removal of the inner pull tab from the metallic cap 12 during opening. Semicircular cut 37 contains a raised portion 35 which allows for placement of a fingernail or the like under the ring on pull tab 16 at the time of opening.

Figure 4:
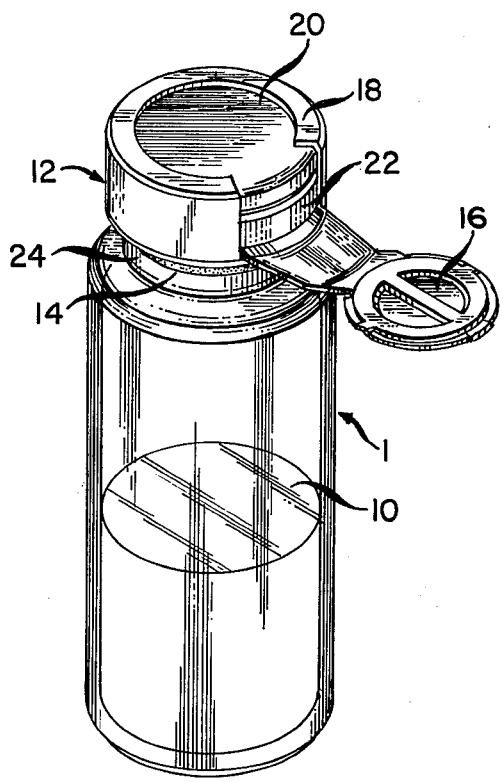
FIG. 4, 5, 6 and 7 illustrate various views of the vial during different stages of opening.

FIG. 4 illustrates a partially opened cap for the vial, 1, found in the kit of the present invention. The pull tab 16 is removed from the cap 12 by first placing a fingernail or the like under the raised portion 35 of semicircular cut 37. Ring or pull tab 16 is detached from the cap 12 by pulling forward thus severing the hinges 33 and bridges at the bottom of cut 32. Placed between metallic cap 12 and plastic stopper 14 is a metallic lid 20. By continued pulling on pull tab 16, the pull tab 16 is completely detached from the cap, 12, leaving the crimped portion of the cap 18 which may easily be removed from the remainder of the lid.

Figure 5:
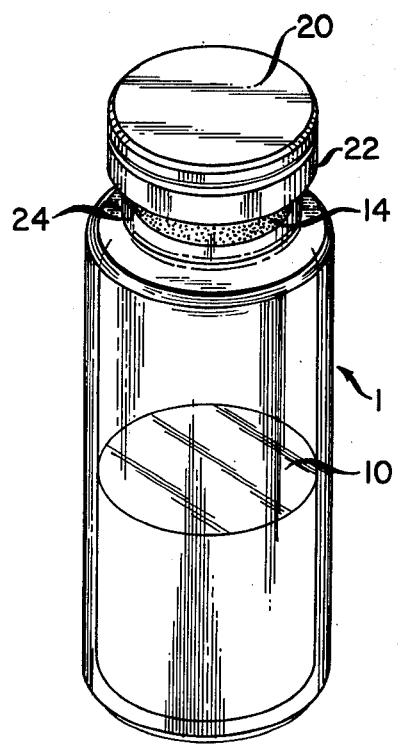

FIG. 5 illustrates the vial of the instant invention after the metallic cap 12 has been completely removed. The mouth of the vial, as defined by rim 22, is still covered by a stopper 14 which is overfitted with a metallic lid 20. The metallic lid 20 may be removed by placing a fingernail or the like between the metallic lid 20 and the stopper 14 and pushing the metallic lid 20 off.

Figure 6:
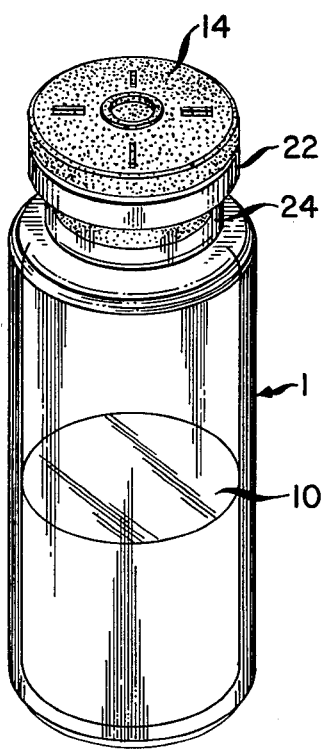

FIG. 6 illustrates the vial of the instant invention after the metallic lid 20 has been removed. The stopper 14 is placed into the mouth of the vial, over the rim 22, and extends downward into the neck 24 of the vial 1. The stopper 14 is removed by placing a finger between the rim 22 and the stopper 14 and pulling the stopper out of the vial.

Figure 7:
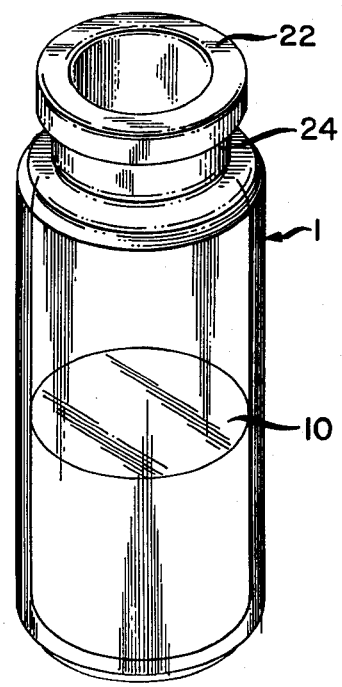

FIG. 7 illustrates a completely opened vial, 1. The vial is partially filled with a lyophilized alpha type interferon formulation 10. A measured amount of distilled water may now be added to the vial to solubilize the formulation. If gentle shaking is necessary, stopper 14 may again be placed into the mouth of the vial 1 so as to avoid any loss of the sample.

FIG. 8 illustrates the various parts of a second component of the kit which is a tube 48 with flexible walls. The squeeze tube 48 contains a neck 45 having outer threads 46 and an opening 47. A lid 36 has inner threads (not shown) for attaching to the outer threads 46 as provided. Lid 36 also contains a dispenser opening 40 formed by the protrusion 42 having outer threads 38. The cap 44 has inner threads (not shown) for attaching to the outer threads 38 as provided.

FIG. 9 illustrates an applicator 49 (in the extended position) suitable for the vaginal application of the alpha type interferon gel formulation. Applicator 49 contains a reservoir member 50 and a plunger 52. The plunger 52 contains a stopper 62 and a flange 54. The plunger may be inserted into the reservoir member at rim 63. Plunger 52 serves as a piston within a cylinder bore defined by reservoir 50.

FIG. 9A illustrates an end view of the applicator 49 taken along the lines 9a—9a of FIG. 9. The reservoir member 50 contains inner threads 60 for attaching the applicator to the outer threads 38 of protrusion 42. The inner thread 60 extend upward into the reservoirs 50 so as to completely mate with outer threads 38.

The reservoir is filled by first attaching the applicator 49 to the tube 48 by mating the outer threads 38 with the inner threads 60. Plunger 52 is then extended from the reservoir 50 while squeezing tube 48 thus filling the reservoir 50 with the alpha type interferon gel formulation contained in the tube. After removing the applicator 49 from the squeeze tube 48, the formulation may then be applied as desired by depressing the plunger, 52, into the reservoir, 50.

FIG. 10 is a sectional view of the vaginal applicator 49 along the section 56—56 in FIG. 9 and illustrates stopper 61. Stopper 61 is fitted at the end of the plunger 52 and contains ribs 62 and protrusion 64. The protrusion 64 extends from the end of the stopper, 61, and is used to facilitate application of the gel formulation. The ribs 62 on stopper 61 are wider than rim 63 of the reservoir, 50, and prevent the removal of the plunger, 52, under normal use. However, in a preferred embodiment, the walls of the reservoir, 50, are sufficiently flexible as to allow the plunger, 52, to be removed from the reservoir, 50, by pulling. This allows the user to readily clean the applicator, 49.

FIG. 11 illustrates a vial 11 having a neck 24 containing outer threads 66. Stopper 14 is placed into the top of the vial. Lid 67 has inner threads (not shown) for attaching to the outer threads 66 as provided. In this embodiment, the vial, 11, is rapidly opened and closed by twisting the lid 67 and removing the stopper 14.

Figure 12:
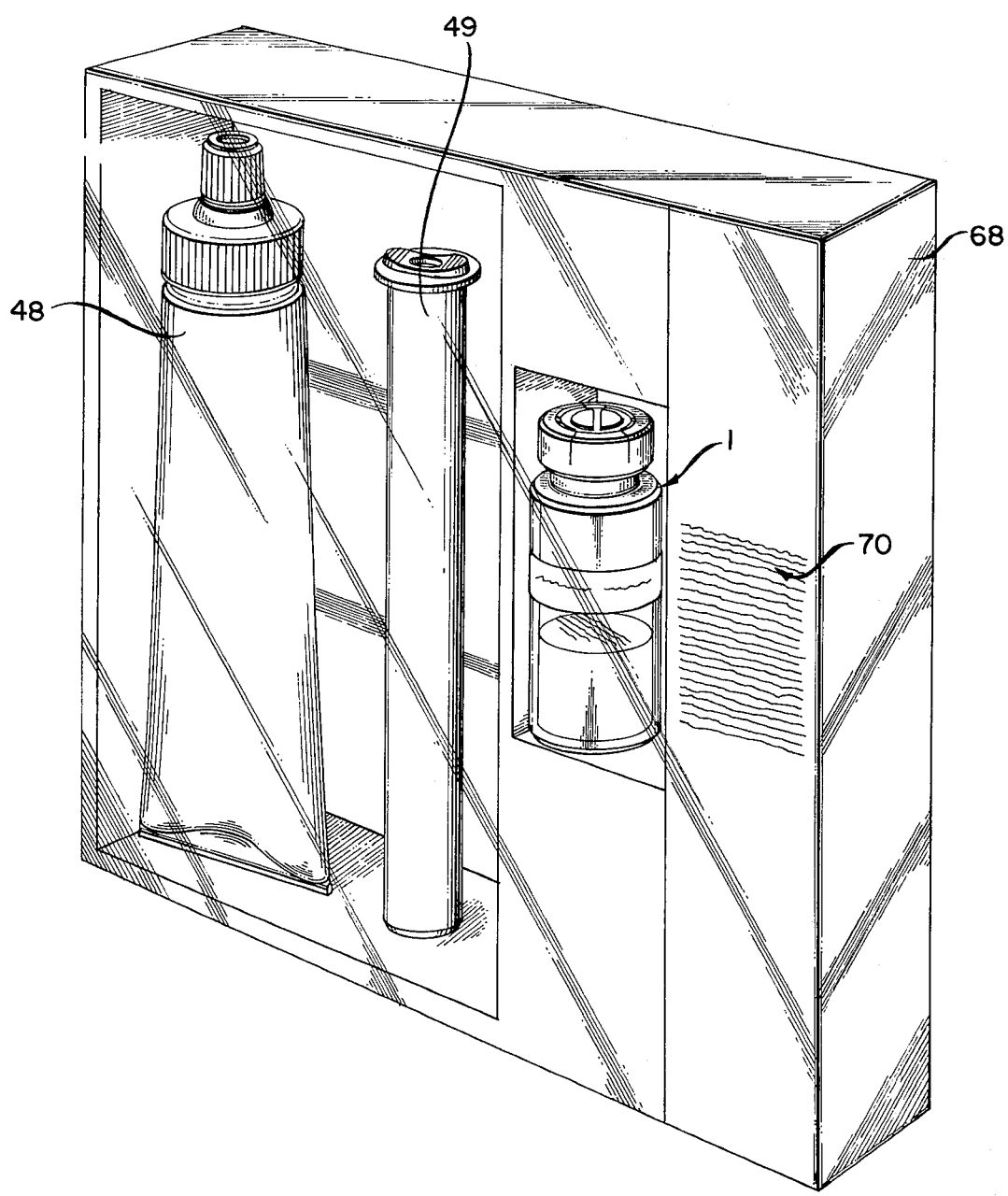
FIG. 12 illustrates a convenient package in which the components of the kit of the instant invention may be stored.

FIG. 12 illustrates one method of packaging the kit of the present invention. The tube with flexible walls 48 together with the applicator 49 if desired are separately stored away from vial 1 in box 68. Optionally, instructions 70 may be provided on the box 68.

We have found that the problem of decomposition of alpha type interferon when employed in topical formulations can be easily and surprisingly eliminated by employing the kit of the instant invention. In particular, we have found that, if the lyophilized alpha type interferon is separately stored and is then added to the pharmaceutical vehicle immediately prior to use the resulting alpha type interferon formulation will retain sufficient activity to insure a therapeutic effect.

The kit of the instant invention may be used to readily prepare at the time of use a lyophilized alpha type interferon gel suitable for topical application. For example, tube 48 is first partially filled with a dermatologically acceptable vehicle which contains a compatible preservative and a sufficient amount of polyoxyethylene polyoxypropylene block polymer for the vehicle to be liquid at about 15° C. or below and to gel at above about 15° C. Lyophilized alpha type interferon 10 may then be solubilized by addition of a measured amount of water to the opened vial 1, opened as described above. The solubilized alpha type interferon formulation 10 may be added to tube 48 at or below 15° C. via opening 47. Lid 36 is then attached to tube 48. Tube 48 is gently shaken to insure homogeneity of the alpha type interferon and then allowed to reach room temperature to form the gel. The gel may then be conveniently dispensed via dispenser opening 40.

A preferred manner of preparing the lyophilized alpha interferon gel formulation using the kit of the instant invention comprises first solubilizing the lyophilized alpha interferon by adding a measured amount of distilled water to the vial containing the lyophilized alpha interferon; adding the resulting solution to a tube with flexible walls containing a dermatologically acceptable vehicle maintained at about 15° C. or below; said vehicle contains a compatible preservative and a sufficient amount of polyoxyethylene polyoxypropylene block polymer for the vehicle to be liquid at about 15° C. or below and to gel at above about 15° C.; forming the gel from the said vehicle plus alpha type interferon solution by allowing the tube to reach a temperature above about 15° C.

By following the above procedure, one may prepare a novel pharmaceutical gel formulation comprising $1 \times 10^4$ to $5 \times 10^8$ International Units of an alpha type interferon formulation prepared from an alpha type interferon having a specific activity of at least $5 \times 10^7$ International Units/mg total protein in a dermatologically acceptable vehicle containing a compatible preservative and a sufficient amount of polyoxyethylene polyoxypropylene block polymer for the vehicle to be a liquid at 15° C. and below and which together with the alpha type interferon gels at 15° C. and above.

In a preferred aspect of the present invention, the tube with flexible walls employed in the kit of the instant invention has a wide opening to allow for the easy addition of the constituted alpha interferon solution. The closure for the tube advantageously possesses a dispenser which allows for a small amount of the gel to be removed from the tube upon squeezing while at the same time closing the wide opening.

Preferably, the dermatologically acceptable vehicle employed in the kit will be stored under refrigeration (2° C. to 8° C.) immediately prior to use. At this temperature the vehicle will be a liquid. Following constitution of the lyophilized interferon with the refrigerated vehicle (liquid state) the system is allowed to achieve room temperature whereupon it forms a gel suitable for topical administration.

The gels employed in the present invention are generally clear in appearance and in addition to the polyoxyethylene polyoxypropylene block polymer may contain any known buffers, skin/mucus permeation enhancers, coloring agents, perfumes and other medicinals.

If an opague gel is desired to give a cream like appearance, 0.1 to 1.0 percent by weight of titanium dioxide may be added to the gel.

In a preferred aspect of the present invention a preservative amount of benzyl alcohol is employed in the dermatologically acceptable vehicle. The concentration of benzyl alcohol which is used is known in the art although in the present invention between 0.5% and 3.0% of benzyl alcohol is generally employed. Other known preservatives such as chlorocresol, methylparaben and the like may be employed in the present formulation in place of benzyl alcohol and are the equivalent to benzyl alcohol.

In order to enhance the effectiveness of benzyl alcohol as a preservative in the present formulation, it is desirable to maintain the formulation at a pH of pH 7 and below. Preferably, a buffer system is employed to maintain the pH at or below pH 7. Phosphoric acid/monobasic sodium phosphate is the preferred buffer system although other known buffer systems are known in the art and may be equally employed. The individual amounts of phosphoric acid and monobasic sodium phosphate employed in the present formulation are generally dependant on the desired pH of the system to be attained.

Likewise, it is preferable not to maintain the pH of system at below pH 2 as the resulting formulation is not pharmaceutical acceptable.

In a preferred aspect of the present invention, the pH of the dermatologically acceptable vehicle is maintained between above pH 2 and pH 4.5 by a phosphoric acid/monobasic sodium phosphate buffer.

The amount of alpha interferon contained in the formulations of the present invention is $1 \times 10^4$ to $5 \times 10^8$ International Units, per gram of gel. Preferably, the amount of alpha interferon contained in the formulations of the present invention is $1 \times 10^6$ to $1 \times 10^8$ I.U. per gram of gel.

Preferably employed in the lyophilized alpha type interferon in the present invention, is an effective amount of glycine which acts as a stabilizer and which is disclosed in U.S. Ser. No. 466,707, the disclosure of which is hereby incorporated herein by reference.

In order to avoid possible side effects and to insure reproducibility of observed therapeutic effects, it is desirable to use alpha type interferons of high specific activity.

The specific activity of alpha type interferon used in the formulations of the present invention should be at least $5 \times 10^7$ International Units/mg total protein. Specific activity may be determined by measuring the antiviral activity as compared to the NIH reference standard and by measuring the total protein content using standard methods (e.g. the Lowry method).

An important aspect of the present invention is the use of an appropriate gelling agent in the dermatologically acceptable vehicle. The gelling agent used must allow for the vehicle to be in a liquid state to allow for constitution of a lyophilized alpha type interferon and in a gel state at room temperature. Additionally, since the gel formulation is to be prepared prior to use by either the pharmacist or an unskilled patient, the gelling agent must be both highly efficient in forming the gel and be easy to handle. Gelling agents possessing these qualities are specific poloxamer compounds, polyoxyethylene-polyoxypropylene block polymers, described in detail by Schmolka et al, U.S. Pat. No. 3,740,421 and incorporated herein by reference and represented by the following formula:

$HO(C_2H_4O)_b (C_3H_6O)_a (C_2H_4O)_b H$ wherein a is an integer such that the hydrophobe represented by $(C_3H_6O)$ has an average molecular weight of from 2250 to 4000 and b is an integer of from 16 to 360.5 such that the hydrophile represented by $(C_2H_4O)$ constitutes from 10 to 90 weight percent of the polymer. The gels of this invention are comprised of from 15 to 90 weight percent polyoxyethylene-polyoxypropylene block polymer. A particularly preferred gelling agent is Poloxamer 407 (Pluronic F-127 available from BASF Wyandotte Corp. of Wyandotte, Mich.) since at appropriate concentrations the gel vehicle is an easily manageable liquid at about 15° C. and below. The lyophilized alpha type interferon is rapidly and uniformly dissolved in the cooled gel vehicle (liquid state) and uniformly mixed by gentle shaking. A preferred aspect of this invention is a kit which allows for a reconstituted solution, e.g., lyophilized alpha interferon constituted with water, to be added to the cooled gel vehicle (liquid state) and be uniformly mixed by gentle shaking. These simple features facilitate preparation of the dosage form at the point of the use and minimize the liklihood of error.

The following non-limiting examples illustrate the kit of the present invention.

EXAMPLE 1

Preparation of the dermatologically acceptable vehicle

| Ingredients | | mg/g |
|---|---|---|
| Poloxamer 407 | | 200.0 |
| Phosphoric Acid NF | | 0.5 |
| Monobasic Sodium Phosphate USP | | 2.94 |
| Benzyl Alcohol NF | | 22.22 |
| Water, Purified USP | q.s. to make | 1.0 g |

The dermatologically acceptable vehicle may be manufactured using either a hot or cold method.

a. Hot Method
1. Heat 90% of the purified water to 80°–90° C.
2. While gently stirring, slowly add the Poloxamer 407 and mix until dissolved.
3. To 5% of the purified water add the phosphoric acid and monobasic sodium phosphate and mix until dissolved.
4. Add Step 3 to Step 2 and mix until homogeneous.
5. Add the benzyl alcohol and mix until homogenous.
6. Bring to final weight with the purified water and mix until the product reaches room temperature.

b. Cold Method
1. Cool 90% of the purified water and maintain its temperature between 4° and 10° C.

Steps 2. through 6. are identical to those used in the Hot Method.

Using either method of manufacture, the formulation is a gel at room temperature.

EXAMPLE 2

Preparation of Alpha-2 Interferon Gel Forumulation

Add an appropriate quantity of the gel vehicle (prepared as in Example 1) from the tube with flexible walls at approximately 10° C. (liguid state) to the vial containing the lyophilized alpha-2 interferon formulation (containing the required interferon dose and having a specific activity of at least $5 \times 10^7$ International Units/mg total protein). Gently shake the vial, bring the system to room temperature, whereupon an elegant gel suitable for topical application is formed.

EXAMPLE 3

The same as Example 1 but the lyophilized interferon formulation is first constituted with one ml of water by addition of the water to the vial. The interferon solution is then added to the tube with flexible walls containing 9 grams of the dermatologically acceptable vehicle, previously cooled to approximately 10° C. Gently shake the tube and bring it to room temperature whereupon the solution forms a gel in the tube with flexible walls.

Likewise by following the procedures outlined in Examples 1 through 3 alpha interferon gel formulation may be prepared by substituting for 200 mg of Poloxamer 407

(a) 150 mg of Poloaxamer 407
(b) 400 mg of Poloaxamer 407
(c) 300 mg of Poloaxamer 355
(d) 600 mg of Poloaxamer 235 and
(e) 400 mg of Poloaxamer 238.

EXAMPLE 4

Similarly, prepare gels of other alpha interferons by substituting alpha-1 or other alpha type interferons for alpha-2 interferon in the above Examples.

The formulations provided for by the kits of the instant invention may be used in the topical treatment of viral skin conditions, e.g., herpes. It is understood, however, that the specific dose level for any particular patient will depend upon a variety of factors including the general health, sex, time of administration and severity of the condition undergoing therapy. Generally, the formulations are applied to the infected area 2 to 4 times daily until no further improvement in the patient's condition is noted.

We claim:

1. A kit for formulating and dispensing an alpha type interferon gel composition comprising (a) a vial having an open end aseptically sealed and containing about $1 \times 10^4$ to $5 \times 10^8$ International Units of lyophilized alpha type interferon formulation prepared from an alpha type interferon having a specific activity of at least $5 \times 10^7$ International Units/mg total protein; (b) and a tube with flexible walls having a sealed open end containing a dermatologically acceptable vehicle which contains a compatible preservative and a sufficient amount of polyoxyethylene polyoxypropylene block polymer for the vehicle to be liquid at 15° C. or below and which together with the lyophilized alpha interferon gels at 15° C. and above.

2. A kit according to claim 1 wherein the lyophilized alpha interferon is alpha-2 interferon.

3. A kit according to claim 2 wherein the compatible preservative employed in the dermatologically acceptable vehicle is benzyl alcohol.

4. A kit according to claim 1 wherein the dermatologically acceptable vehicle additionally contains a compatible buffer system to maintain the pH of the composition from pH 2 to pH 7.

5. A kit according to claim 4 wherein the compatible buffer sytem is phosphoric acid/monobasic sodium phosphate.

* * * * *